US006280723B2

(12) United States Patent
Stimac et al.

(10) Patent No.: US 6,280,723 B2
(45) Date of Patent: *Aug. 28, 2001

(54) METHODS AND MATERIALS FOR CONTROL OF TERMITES

(75) Inventors: Jerry L. Stimac, Gainesville, FL (US); Sérgio Batista Alves, Sao Paulo (BR)

(73) Assignee: University of Florida, Gainesville, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/156,011

(22) Filed: Sep. 17, 1998

Related U.S. Application Data

(60) Provisional application No. 60/059,104, filed on Sep. 17, 1997.

(51) Int. Cl.$^7$ .......................... A01N 63/04; A01N 25/00; A01N 25/08; A01N 25/34

(52) U.S. Cl. .................. 424/93.5; 424/405; 424/408; 424/409; 424/410; 435/254.1

(58) Field of Search .................................. 424/93.5, 405, 424/408, 409, 410; 435/254.1

(56) References Cited

U.S. PATENT DOCUMENTS

| | | |
|---|---|---|
| 4,626,528 | 12/1986 | McHenry . |
| 4,925,663 | 5/1990 | Stimar . |
| 5,151,443 | 9/1992 | Henrick . |
| 5,683,689 | * 11/1997 | Stimac et al. ........................ 424/93.5 |
| 5,728,573 | * 3/1998 | Sugiura et al. ................... 435/254.1 |
| 5,888,989 | * 3/1999 | Kern ....................................... 514/63 |

FOREIGN PATENT DOCUMENTS

| | | |
|---|---|---|
| 2731318 | 3/1996 | (FR) . |
| 09404034 | * 3/1994 | (WO) . |

OTHER PUBLICATIONS

Alves, S.B. et al. (1995) "Use of Metarhizium anisopliae and Beauveria bassiana for control of Cornitermes cumulans (Kollar, 1832) in pastures" Ecossistema 20:50–57 (** abstract only).

Almeida, J.E. et al. (1997) "Selection of *Beauveria spp.* Isolates for control of the termite *Heterotermes tenuis*" Jounral of Applied Entomology 121(9–10):538–543 (abstract only).

Alves, S.B. et al. (1997) "Termiticidal baits" Chemical Abstracts 127(23) (** abstract only).

Jones, W. E. et al. (1996) Virulence of seven isolates of Beauveria Bassiana and Metarhizim anisopliae to Coptotermes formosanus 25(2):481–487 (**abstract only).

Delate, K.M. et al. (1995) "Potential use of pathogenic fungi in baits to control the Formosan subterranean termite (Isopt., Phinotermitidae" Journal of Applied Entomology 119(6):429–433 (** abstract only).

Wells, J.D. et al. (1995) Virulence of four fungal pathogens to Coptotermes formosanus (Isoptera: Rhinotermitidae) Journal of Entomological Science 30(2):208–215 (**abstract only).

Zoberi, M.H., J.K. Grace (1990) "Isolation of the pathogen bassiana from *Reticulitermes flavipes* (Isoptera: Rhinotermitidae)" Sociobiology 16(3):289–296 (**abstract only).

Grace, J.K. et al. (1993) "Microbial termite control: effects of entomogenous fungi on the Formosan subterranean termite (Isoptera: Rhinotermitidae)" Proceedings of the 1$^{st}$ International Conference on Insect Pests in the Urban Environment, p. 474 (*abstract only).

Grace, J.K. et al. (1993) "Microbial Termite Control: Effects of Entomogenous Fungi on the Formosan Subterranean Termite (Isoptera: Rhinotermitidae)," Proceedings of the 1$^{st}$ International Conference on Insect Pests in the Urban Environment, p. 474.

Alves, S.B. et al. (1995) "Use of Metarhizium anisopliae and Beauveria bassiana for control of Cornitermes cumulans (Kollar, 1832) in Pastures," *Ecossistema* 20:50–57 (certified translation).

Delate, K.M. et al. (1995) "Potential Use of Pathogenic Fungi in Baits to Control the Formosan Subterranean Termite (Isopt.,Rhinotermitidae)" *J. Appl. Ent.* 119:429–433.

Jones, W.E. et al. (1996) "Virulence of Seven Isolates of *Beauveria bassiana* and *Metarhizium anisopliae* to *Coptotermes formosanus* (Isoptera; Rhinotermitidae)" *Entomological Society of America* 25(2):481–487.

Wells, J.D. et al. (1995) "Virulence of Four Fungal Pathogens to *Coptotermes formosanus* (Rhinotermitidae)" *J. Entomol. Sci.* 30(2):208–215.

Zoberi, M.H. et al. (1990) "Isolation of the Pathogen *Beauveria bassiana* from *Reticulitermes flavipes* (Isoptera: Rhinotermitidae)" *Sociobiology* 16(3):289–296.

Hänel, H. (1982) "Selection of a fungus species, suitable for the biological control of the termite *Nasutitermes exitiosus* (Hill)" *Z. ang. Ent.* 94:237–245.

Su, Nan–Yao, Rudolf H. Scheffrahn (1990) "Potential of Insect Growth Regulators as Termiticides: A Review" *Sociobiology* 17(2):313–328.

(List continued on next page.)

Primary Examiner—Christopher R. Tate
(74) *Attorney, Agent, or Firm*—Saliwanchik, Lloyd & Saliwanchik

(57) ABSTRACT

The subject invention provides for a method for controlling termites by contacting the termites with a composition comprising *Beuveria bassiana* No. 447 (ATCC 20872).

17 Claims, 1 Drawing Sheet

OTHER PUBLICATIONS

Figure 1:
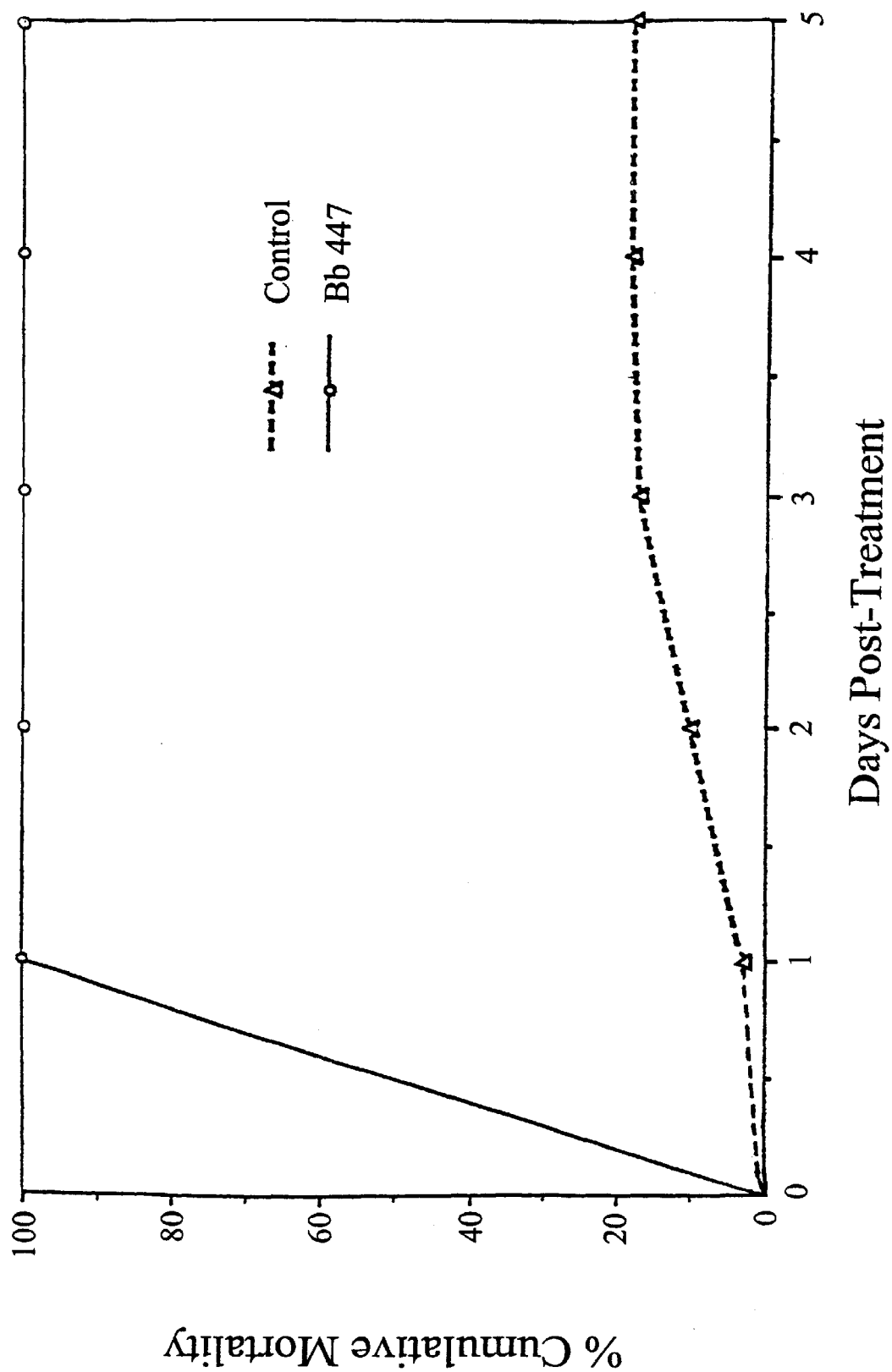

Su, Nan–Yao, Rudolf H. Scheffrahn (1988) "Toxicity and Lethal Time of N–Ethyl Perfluorooctane Sulfonamide Against Two Subterranean Termite Species (Isoptera:Rhinotermitidae)" *Florida Entomologist* 71(1):73–78.

Hanel, H., J.A.L. Watson (1983) "Preliminary field tests on the use of *Metarhizium anisopliae* for the control of *Masutitermes exitiosus* (Hill) (Isoptera:Termitidae)" *Bull. ent. Res.* 73:305–313.

Smythe, R.V., H.C. Coppel (1965) "The Susceptibility of *Reticulitermes flavipes* (Kollar) and Other Termite Species to an Experimental Preparation of *Bacillus thuringiensis* Berliner" *J. of Invertebrate Pathology* 7:423–426.

Yendol, William G., John D. Paschke (1965) "Pathology of an *Entomophthora* Infection in the Eastern Subterranean Termite *Reticulitermes flavipes* (Kollar)" *J. of Invertebrate Pathology* 7:414–422.

Su, Nan–Yao, Rudolf H. Scheffrahn (1991) "Laboratory Evaluation of Two Slow–Acting Toxicants Against Formosan and Eastern Subterranean Termites (Isoptera:Rhinotermitidae)" *J. of Economic Entomology* 84(1):170–175.

Su, Nan–Yao (1991) "Evaluation of Bait–Toxicants for Suppression of Subterranean Termite Populations" *Sociobiology* 19(1):211–220.

Lai, P. Y., M. Tamashiro, J. K. Fujii (1982) "Pathogenicity of Six Strains of Entomogenous Fungi to *Coptotermes formosanus*" *J. of Invertebrate Pathology* 39:1–5.

Su, Nan–Yao, Rudolf H. Scheffrahn (1989) Comparative Effects of an Insect Growth Regulator, S–31183, Against the Formosan Subterranean Termite and Eastern Subterranean Termite (Isoptera:Rhinotermitidae) *J. of Economic Entomology* 82(4):1125–1129.

Su, Nan–Yan, Minoru Tamashiro, Michael I. Haverty (1987) "Characterization of Slow–acting Insecticides for the Remedial Control of the Formosan Subterranean Termite (Isoptera:Rhinotermitidae)" *J. of Economic Entomology* 80(1):1–4.

Jones, Susan C. (1984) "Evaluation of Two Insect Growth Regulators for the Bait–Block Method of Subterranean Termite (Isoptera:Rhinotermitidae) Control" *J. of Economic Entomology* 77(5):1086–1091.

Kramm, Kenneth R., David F. West (1982) "Termite Pathogens: Effects of Ingested Metarhizium, Beauveria, and Gliocladium Conidia on Worker Termites (Reticulitermes sp.)" *J. of Invertebrate Pathology* 40:7–11.

Kimbrough, James W. (1982) "Structure and Development of *Mattirolella Crustosa* (Termitariales, Deuteromycetes) on Panamanian Termites" *mycologia* 74(2):201–209.

Beal, R. H., A. G. Kais (1962) "Apparent Infecton of Subterranean Termites by *Aspergillus flavus* Link" *J. Invert. Path.* 4:488–489.

* cited by examiner

METHODS AND MATERIALS FOR CONTROL OF TERMITES

CROSS-REFERENCE TO RELATED APPLICATION

This application claims priority from provisional application U.S. Ser. No. 60/059,104, filed Sep. 17, 1997.

BACKGROUND OF THE INVENTION

The annual estimated costs of termite damage and control in the United States increased from $100 million in 1967 to $1.02 billion in 1986. Among the 30 species of termites reported to be of economic importance in the U.S., five species are considered to have the most significant impact, partly because of their wide distribution. These species include the drywood, or powderpost, termites *Cryptotermes brevis*, in the southeastern U.S. and Hawaii, and Incisitermes minor, which is found in Texas, the southwest, and in the Rocky Mountains and westward. The remaining three species are the subterranean termites *Coptotermes formosanus*, in the southeast and Hawaii, *Reticulitermes hesperus* in the northwest and California, and *R.flavipes* throughout the U.S. east of the Rocky Mountains. In addition to the termites listed above, other species may cause significant damage in more localized areas.

Subterranean termites most often enter structures from the surrounding soil to feed on wood, or other cellulosic material, of the structure and its contents. Subterranean termites construct an extensive foraging gallery beneath the soil surface. A single colony may contain several million termites with foraging territory extending up to 300 feet (Su, N.Y., R. H. Scheffrahn [1988] *Sociobiol.* 14(2):353–359). Since subterranean termites are cryptic creatures, their presence is not normally known until after some damage, foraging tubes, or live termites such as swarmers, are found. Some subterranean termites are known to forage beneath an object on the soil surface (Ettershank,G., J. A. Ettershank, W. G. Whitford [1980] *Environ. Entomol.* 9:645–648).

Control methods for structural infestations of termites varies with the ecology of the different species. Currently, there are two basic approaches for the control of subterranean termites: preventive control and remedial control. In general, preventive measures include the use of wood treated with various repellant chemicals; metal shields between the foundation supports and buildings that either act as barriers, or as a detection method when termites construct visible tubes around the shields; and the creation of chemical barriers by treating the soil under the building foundation, before and after construction, with long-residual termiticides. A layer of basaltic rock particles placed under foundations has been used as a physical barrier to stop the penetration of subterranean termite tunneling. Removal of lumber scraps and sites that accumulate water also discourage the establishment of termite colonies.

Remedial control methods can entail removal of infested wood and replacement with treated wood; drilling and injecting insecticides into small, localized infestations; fumigation of structures with widespread infestations; and use of slow-acting insecticides (Su, N.-Y., M. Tamashiro, and M. 1. Haverty (1987) *J. Econ Entomol.* 80:1–4). Aerial colonies of *C.formosanus* can be eliminated by the removal of their moisture source. Post-construction soil application of termiticides to eliminate subterranean termite colonies, while commonly attempted, is of limited success (Su, N.-Y., and R. H. Scheffrahn (1990a) *J. Econ. Entomol.* 83:1918–1924).

In some of the United States, it is mandatory that the soil underlying the foundation of newly constructed buildings be pre-treated with a termiticide to prevent termite infestation. Pesticide is typically sprayed over and into the soil prior to construction. This pre-construction treatment produces a horizontal barrier beneath the building. Because of the lack of communication between pesticide applicator and construction workers, the barrier often loses its continuity during the construction. Moreover, the currently available soil termiticides tend to lose their biological activity after five or more years to the extent that the treated soil is no longer effective against termite invasion. Established termite colonies in the soil may then invade the structure if additional chemical is not applied beneath and around the structure.

When a house or other building is infested by subterranean termites, efforts are made to create a continuous barrier beneath the building in the soil where the subterranean termites are provided access to the building. A common method of creating this barrier is to introduce termiticide around a building foundation by injection into soil underlying concrete foundations, drenching the soil surrounding the building perimeter, or a combination of both. This type of post-construction treatment is labor-intensive and may not adequately produce a continuous barrier (Frishman, A. M., B. L. Bret [1991] *Pest Control* 59(8):48, 52, 54, 56; Frishman, A. M., A. St. Cyr [1988] *Pest Control Technology* 16(4):33, 34, 36).

Other remedial treatments include spot treatments such as dusting or injecting termiticides within the walls of the building. Robert Verkerk has described arsenic trioxide dust treatment using termite lures (Verkerk, R. [1990] *Building Out Termites*, Pluto Press Australia Limited, P.O. Box 199, Leichhardt, NSW 2040). Verkerk describes the use of stakes or blocks of termite susceptible timber to lure termites after the stakes or blocks have been placed near a known termite problem. Once termite activity is observed, arsenic trioxide is injected. Alternatively, a portion of the termites may be dusted with arsenic trioxide.

The effectiveness of the former standard soil termiticides, chlordane and heptachlor, precluded substantial research in alternative termite control methods. Since their withdrawal from the market in 1987, replacement termiticides include chlorpyrifos (Dursban TC) and isofenphos (Pryfon 6), cypermethrin (Demon TC), permethrin (Dragnet FT), fenvalerate (Tribute) and imidacloprid(Premise). Given the loss of chlordane and heptachlor, alternative control measures, such as the use of toxicant and insect growth regulator baits, are being researched (Su, N.-Y., and R. H. Scheffrahn (1990b) *Sociology* 17:313–328).

A wide variety of termite control methods have been proposed. Japanese patent applicationNos. 61-198392 and 63-151033 describe wooden vessels specifically designed to "attract" termites as part of a monitoring procedure. In the 63-151033 application, the termites are further exposed to a toxicant which is then presumably carried back to the nest in hopes of killing the queen via trophallaxis or food exchange.

Australian Patent No. 1,597,293 (the '293 patent) and a corresponding Great Britain Patent, No. 1,561,901, describe a method which involves mixing insecticide with a food matrix comprising cellulose and a binding agent.

One termite control method comprises placing a highly toxic material, such as an arsenic-containing dust, at a site of infestation in the hope that this will directly control an effective number of termites at the site and also other termites back in the colony.

Elaborate schemes of pipes to convey liquid termiticides under and surrounding buildings have also been proposed for termite control. It has been suggested that these liquid termiticides may be dispensed into the soil surrounding and below the building through these pipes to provide a continuous barrier to the incursion of termites. This method requires a large quantity of termiticides in order to saturate the soil surrounding the building.

U.S. Pat. No. 5,027,546 describes a system intended for use on above ground termites, i.e., drywood termites, which controls termites by freezing with liquid nitrogen. U.S. Pat. No. 4,043,073 describes a method which attempts to circumvent the problem of repeated application of pesticide. The described method functions by "encapsulating" the insecticide, thus making it more persistent. The overt use of pesticides and their persistence in the environment are not remedied by this system. Another proposed system which fails to alleviate the problem of transferring insecticide directly into the soil is U.S. Pat. No. 3,624,953. This method employs a reservoir of insecticide wherein the vapors of the insecticide are permitted to permeate the soil surrounding the reservoir. Thus, exposure of the environment with toxic substances is not avoided by using this method.

Toxicants which have less environmental effect and which show activity against termites are known (Su, N.Y., M. Tamashiro, M. Haverty [1987] *J. Econ. Entomol.* 80:1–4; Su, N.Y., R. H. Scheffrahn [1988] *Florida Entomologist* 71(1):73–78; Su, N.Y., R. H. Scheffrahn [1989] *J. Econ. Entomol.* 82(4):1125–1129; Su, N.Y., R. H. Scheffrahn [1990b] *Sociobiol* 17(2):313–328; Su, N.Y. [1991] *Sociobiol.* 19(1):211–220; Su, N.Y., R. H. Scheffrahn [1991] *J. Econ. Entomol.* 84(1):170–175; Jones, S. [1984] *J. Econ. Entomol.* 77:1086–1091; Paton,R., L. R. Miller [1980] "Control of *Mastotermes darwiniensis* Froggatt (Isoptera: Mastotermitidae) with Mirex Baits," *Australian Forest Research* 10:249–258; McHenry, W. E., U.S. Pat. No. 4,626,528; Henrick, C. A., U.S. Pat. No. 5,151,443).

It should be noted that attractants other than water for termites have been investigated. For example, the extract from brown-rot fungi chemically resembles the trail-following pheromones of termites. Natural pheromones, however, are species- and even colony-specific. A pheromone that is "attractive" to one species or colony of termites may repel termites of other species or colonies. It is of uncertain value, therefore, to incorporate pheromone mimics (such as the brown-rot fungi extract) in a bait, especially if a bait is to be used against a wide range of termite species.

Reported natural enemies of termites consist of general predators such as birds, lizards, spiders, ants, and centipedes. Parasitic mites are known to parasitize termites in laboratory colonies. Phorid and calliphorid flies have been reported as parasitoids of African and southeast Asian termites. Insect parasitoids of North American termites have not been recorded. Nematodes have been found in termites, and a few species have been evaluated as potential control agents. However field efficacy by these nematodes was not adequate.

Several microbial pathogens have been isolated from termites (Sands, W. A. (1969) "The association of termites and fungi, pp. 495–524, In K. Krishna & M. F. Weesner [eds.] Biology of Termites Vol.I, Academic Press, New York; Beal, R. H. and A. G. Kais (1962) *J. Invert. Path.* 4:488–489; Kimbrough, J. W. and B. L. Thome (1982) *Mycologia* 74:201–209. Bioassays of *Metarhiziu-manisopliae* (Hanel, H. (1982) *Z. ang. Ent.* 94:237–245; Lai, P. Y., M. Tarnashiro, J. K. Fujii (1982) *J. Invert Path.* 39:1–5; Fernandes, P. C. (1991) Microbial control of *Cornitermes cumulans* (Kollar, 1832) (Isoptera-Termitidae) with *Beauveria bassiana* (Bals.) Vuill. and *Metarhizium anisopliae* (Metsch.) Sorok., Ph.D. dissertation. Univ. São Paulo, Piracicaba, 114 p.; *Beauveria bassiana* (Lai et aL (1982) supra; Fernandes (1991) supra; *Gliocladium virens* (Kramm, K. R., D. F. West (1982)*J. Invert. Path.* 40:7–11; species of *Entomophthora* (Yendol, W. G. and J. D Paschke (1965)*J. Invert. Path.* 7:414–422; Hanel(1982) supra, and *Bacillus thuringiensis* (Smythe, R. V. and H. C. Coppel (1965) *J. Invert. Pathol.* 7:423–426) have all shown that termite mortality can occur under laboratory conditions. A field application of *M. anisopliae* resulted in recoveries of infected termites, but it did not eliminate the colonies (Hanel and Watson 1983). While potential for microbial control is evident in the laboratory, efficacy under field conditions has generally been lacking. A United States patent has been granted for a fungus showing high activity against fire ants, U.S. Pat. No. 4,925,663. This isolate, designated *Beauveria bassiana* isolate No. 447, was deposited in a public repository. This isolate is also active against cockroaches (WO 95/25430). The subject invention concerns the new use of *B. bassiana* No. 447 for control of termites.

BRIEF SUMMARY OF THE INVENTION

The invention disclosed and claimed herein relates to a method for controlling termites. Specifically,the subject invention concerns the use of a highly virulent *Beauveria bassiana* isolate to control termites. Specifically exemplified herein are formulations containing *B. bassiana* isolate No. 447. This isolate advantageously shows unexpectedly high virulence against termites and does not produce the environmental hazards associated with chemical control agents.

The fungal biopesticides described herein can be applied to termites in their normal habitats. The fingus may be applied, for example, directly to the termites, or applied to their surroundings, or anywhere that termites are a problem. In a preferred embodiment, the fungus is applied alone to termites through a bait but also could be applied in conjunction with other agents that cause stress on individuals or the colony.

The subject invention also includes mutants of the exemplified isolate which substantially retain the high virulence of the parent strain.

BRIEF DESCRIPTION OF THE DRAWING

FIG. 1 shows cumulative percent mortality of subterranean termites exposed to *B. bassiana* isolate No. 447.

DETAILED DESCRIPTION OF THE INVENTION

The subject invention concerns the use of fungal biocontrol agents to control termites. Specificallyexemplified herein is the use of *Beauveria bassiana* isolate No. 447 to control subterranean termites.

A biologically pure culture of *Beauveria bassiana* No. 447 has been deposited in the American Type Culture Collection (ATCC), 12301 Parklawn Drive, Rockville, Md. 20852 in conjunction with U.S. Pat. No. 4,925,663. The deposit information and accession numbers are as follows:

| Culture | Accession Number | Deposit Date |
|---|---|---|
| *Beauveria bassiana* No. 447 | ATCC 20872 | December 29, 1987 |

The entomopathogenic fungus *Beauveria bassiana* (Bals.) Vuill. is a Deuteromycota: Hyphomycetes. The genus Beauveria Vuill. is distinguished from other genera by having conidigenous cells with an apical denticulate root with zig-zag appearance. Conidia are globulose to subglobulose, equal to or less than 3.5 micrometers in diameter. The sexual stage is probably Cordyceps. The species *Beauveria bassiana* has spherical, not ellipsoid, conidia with conidiophores forming dense bunches.

Formulations. In a preferred embodiment, the formulation comprises a bait having the fungal biocontrol agent and a food component. Optionally, the formulation may also comprise an attractant. The preferred formulation is non-repellantand includes a food source so that termites will forage and recruit other nestmates for foraging activity. In a preferred embodiment, the formulation of the subject invention advantageously adheres to the body of the termite, thereby facilitating colonization of the pest by the fungal biocontrol agent.

In one embodiment of the subject invention *B. bassiana* isolate is applied in conjunction with another termiticide. Preferably, the other termiticide is applied at a concentration or rate which, if used alone, does not result in complete control of the termites. Thus, the activity of *B. bassiana* together with sub-lethal doses of a tertniticide can be used to achieve effective termite control.

Following are examples which illustrate procedures, including the best mode, for racticing the invention. These examples should not be construed as limiting. All percentages are by weight and all solvent mixture proportions are by volume unless otherwise noted.

EXAMPLE 1
Preparation of the Fungus

The subject fungus can be produced in trays with a rice-based medium. An isolate of fungal inoculum is used to initiate the growth of the fungus in the trays.

The initial inoculum is prepared in petri dishes. The pure spores are then transferred into jars containing sterile white rice without skins.

The medium for the trays is prepared as follows:

1. The rice is pre-cooked for 10 minutes.
2. 750 grams of cooked rice is placed in polyethylene bags and sterilized in an autoclave at 120° C. for 30 minutes.
3. Within a laminar flow hood, one teaspoon of spores and rice from the inoculum jars is added to each bag of prepared sterile medium.
4. Each bag is closed tightly by folding and stapling the open end.
5. The bags are transferred to a sterile room with positive pressure, temperature at 24.0–27.0° C., relative humidity above 70%, and 16 hours photophase. This room is known as the "environment room."

After 3 days in the environment room, bags containing mycelia are selected and their contents are transferred to plastic trays. The size of the trays is such that each tray will accommodate the contents of 2–3 bags. The trays and their contents are left in the environment room for 8–10 days. At the end of the 8–10 day period, the trays are transferred to a room with a cool (0–20° C.) current of clean air. The trays are left in this room until the cool air has dried the rice and fingus mixture.

The uncontaminated trays of rice covered with fungus can be harvested and prepared for application or storage. If the fungus will be applied to termites within 1–2 weeks after production, conidia can be collected by shaking and sieving. The resulting powder contains spores and some mycelia, and can be applied directly to termites or used to prepare a formulation as a liquid, powder, or bait.

If the fungus is to be stored for a short period of time, the mixture can be mixed with cornstarch or talc and placed into sterile plastic containers sealed tightly and stored in a refrigerator at 4° C. or in a room with a temperature range of 10–25° C. and no direct sunlight. A temperature of –7° C. is better for longer storage times. The high virulence of *B. bassiana* can be compromised by bacterial or fungal contamination. Therefore, throughout the preparation of the fungus, great care must be taken to maintain the sterility of all instruments and equipment.

The fingus-containing product can be applied to termites and their nests as a liquid, powder, or put out as a baited trap for the termites to forage, become infected, and carry inoculum back to the nest.

EXAMPLE 2
Spray Application

Spraying can be used for treating individual termites or small groups of these pests. A fungal suspension containing $1.0 \times 10^7$ to $1.0 \times 10^9$ spores per milliliter of water can be sprayed on the termites using an airbrush or other means as an applicator.

EXAMPLE 3
Powder Application

A fungal spore and mycelia mixture can be mixed with cornstarch or talc and applied to the pests' surroundings as a dry powder.

The powder is prepared as in Example 1 above. The sieved *B. bassiana* powder which contains the rice, spores, and mycelia is mixed with cornstarch or talc. Application of this powder to the nests or directly to the pests can facilitate rapid and widespread fungal growth within the nest or on the pest.

The application can be accomplished using a pressurized air applicator with an attachment that distributes the mixtures into cracks and crevices of a termite-inhabited building. During and following application, termites covered with white powder will be observed. These infected pests will die within 1–5 days, and the spores they produce will be infective to other termites. Active spores will remain in the surroundings at the nest site, thereby providing inoculum to infect other termites.

EXAMPLE 4
Baited Trap Application

In a preferred embodiment, the fungal powder can be used in a trap in which entryways are laced with fungal inoculum. Preferably, fungal spores are utilized. A bait attractant contained within the trap will be foraged by termites and the foragers will become infected. These infected individuals will return to the nest and thereby introduce the fungal disease into the nest. Various attractants, including pheromone compounds, are well known to those skilled in this art. A quantity of 0.5–2.0 grams of fungal mixture containing spores and mycelia should be contained in each trap. The number of traps used in an area will depend on the level of infestation.

EXAMPLE 5

Control of Termites with *B. bassiana* No 447.

Termites (*Reticulitermes* spp.) were treated with *B. bassiana* 447. Using a spray tower, conidial suspensions were applied to four or five replicates of 20 worker termites. Daily mortalities were recorded for 15 days and were collected daily, surface sterilized and plated to determine levels of sporulation.

Tests were also conducted with powder formulations consisting of 1 or 10% conidia of different fungal isolates. Twenty Reticulitermes termites were placed in each of 5 petri dishes containing 0.02 g of the formulations. After a 24-h exposure period, the insects were transferred to plastic containers and were observed daily. Cadavers were removed, surface sterilized and plated to allow development of infecting fungi.

When formulations containing 10% of conidiain cornstarch were used, mortality of the insects occurred at high levels at 1–2 days after treatment for all strains of fungi tested (FIG. 1). *B. bassiana* isolate 447 killed all the treated insects by the second day after initial exposure to fungal material.

Because the powder formulations were so efficient in the first test against termites, a second experiment was conducted with lower doses of the fungi. Total mortality of termites was also obtained when insects were exposed to formulations containing 1% conidia of the fungal isolates. Mortality increased at a slower rate than when the 10% formulations were used, however, all insects died within 5 days after treatment. Mortality peaked at 3 days after treatment. Sporulation on cadavers was about 88%.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for controlling termites, said method comprising contacting said termites with a composition comprising *Beauveria bassiana* No. 447 (ATCC 20872) and said termites are of the genus Cryptotermes, Incisitermes, Coptotermes, or Reticulotermes.

2. The method, according to claim 1, wherein said *Beauveria bassiana* is incorporated into a bait.

3. The method, according to claim 2, wherein said bait comprises a food source for termites.

4. The method, according to claim 1, wherein said *Beauveria bassiana* is applied as a liquid spray.

5. The method, according to claim 1, wherein said *Beauveria bassiana* is applied as a powder.

6. The method according to claim 1, wherein said termites are of the genus Cryptotermes.

7. The method according to claim 1, wherein said termites are of the genus Incisitermes.

8. The method according to claim 1, wherein said termites are of the genus Coptotermes.

9. The method according to claim 1, wherein said termites are of the genus Reticulotermes.

10. The method according to claim 1, wherein said termites are of the species *Cryptotermes brevis*.

11. The method according to claim 1, wherein said termites are of the species *Incisitermes minor*.

12. The method according to claim 1, wherein said termites are of the species *Coptotermes formosanus*.

13. The method according to claim 1, wherein said termites are of the species *Reticulotermes flavipes*.

14. The method according to claim 1, wherein said composition further comprises an attractant.

15. The method according to claim 1, wherein said composition further comprises a food source.

16. The method according to claim 1, wherein said composition further comprises additional termiticide.

17. The method according to claim 1, wherein said composition further comprises sub-lethal concentrations of additional termiticide.

* * * * *

UNITED STATES PATENT AND TRADEMARK OFFICE
CERTIFICATE OF CORRECTION

PATENT NO. : 6,280,723 B1
DATED : August 28, 2001
INVENTOR(S) : Jerry L. Stimac and Sergio Batista Alves It is certified that error appears in the above-identified patent and that said Letters Patent is hereby corrected as shown below:

Column 1,
Line 22, "*R.flavipes*" should read -- *R.. flavipes* --.
Line 38, "(Ettershank,G.," should read -- (Ettershank, G., --.
Line 61, "M. 1." should read-- M.I. --.
Line 61, "*Econ*" should read -- *Econ.* --.
Line 62, "*C.formosanus*" should read -- *C. formosanus* --.

Column 3,
Line 33, "Paton,R.," should read -- Paton, R., --.
Line 62, "Vol. I," should read -- Vol. I, --.
Line 64, Thome" should read -- Thorne --.
Line 67, Tarnashiro," should read -- Tamashiro, --.
Line 67, "*J. Invert*" should read -- *J. Invert.* --.

Column 4,
Line 7, "(1982)*J.*" should read -- (1982) *J.* --.
Line 9, "(1965)*J.*" should read -- (1965) *J.* --.
Line 9, "Hanel(1982)" should read -- Hanel (1982) --.
Lines 14-15, "(Hanel and Watson 1983)." should read -- (Hanel, H. and J.A.L. Watson (1983) "Preliminary field tests on the use of *Metarhizium anisopliae* for the control of *Nasutitermes exitiosus* (Hill) (Isoptera: Termitidae). *Bull. Ent. Res.* 73:305-313). --.
Line 18, "generally been lacking. A Unites States" should read -- generally been lacking.
      A United States --.
Line 29, "Specificaly,the" should read -- Specifically, the --.
Line 38, "fingus" should read -- fungus --.
Line 59, "Specificallyexemplified" should read -- Specifically exemplified --.

UNITED STATES PATENT AND TRADEMARK OFFICE
CERTIFICATE OF CORRECTION

PATENT NO.    : 6,280,723 B1
DATED         : August 28, 2001
INVENTOR(S)   : Jerry L. Stimac and Sergio Batista Alves It is certified that error appears in the above-identified patent and that said Letters Patent is hereby corrected as shown below:

Column 5,
Line 32, "tertniticide" should read -- termiticide --.
Line 35, "racticing" should read -- practicing --.

Column 6,
Line 2, "(0-20° C.)" should read -- (10-20°C) --.

Column 7,
Line 17, "conidiain" should read -- conidia in --.

Signed and Sealed this

Sixteenth Day of April, 2002

Attest:

JAMES E. ROGAN
Attesting Officer        *Director of the United States Patent and Trademark Office*